(12) United States Patent
Palagi et al.

(10) Patent No.: US 10,568,673 B2
(45) Date of Patent: Feb. 25, 2020

(54) LAMINAR CLAMP TENSIONER AND METHOD

(71) Applicant: Life Spine, Inc., Huntley, IL (US)

(72) Inventors: Gregory Palagi, Geneva, IL (US); Michael S. Butler, St. Charles, IL (US)

(73) Assignee: LifeSpine, Inc., Huntley, IL (US)

( * ) Notice: Subject to any disclaimer, the term of this patent is extended or adjusted under 35 U.S.C. 154(b) by 0 days.

(21) Appl. No.: 15/950,146

(22) Filed: Apr. 10, 2018

(65) Prior Publication Data

US 2018/0289405 A1    Oct. 11, 2018

Related U.S. Application Data

(60) Provisional application No. 62/483,762, filed on Apr. 10, 2017.

(51) Int. Cl.
| A61B 17/70 | (2006.01) |
| A61B 17/84 | (2006.01) |
| A61B 17/88 | (2006.01) |
| A61B 17/00 | (2006.01) |

(52) U.S. Cl.
CPC ........ *A61B 17/842* (2013.01); *A61B 17/7053* (2013.01); *A61B 17/8869* (2013.01); *A61B 2017/00367* (2013.01); *A61B 2017/00477* (2013.01)

(58) Field of Classification Search
CPC ............ A61B 17/7053; A61B 17/7083; A61B 17/842; A61B 17/8869; A61B 17/8861
USPC ....................................................... 606/263
See application file for complete search history.

(56) References Cited

U.S. PATENT DOCUMENTS

| 9,173,685 B2 * | 11/2015 | Lindquist ........... A61B 17/7049 |
| 2005/0131404 A1 | 6/2005 | Mazda et al. |
| 2012/0022592 A1 | 1/2012 | Belliard |
| 2012/0271354 A1 | 10/2012 | Baccelli et al. |

(Continued)

FOREIGN PATENT DOCUMENTS

| EP | 2 047 813 A1 | 4/2009 |
| EP | 2777569 A1 | 9/2014 |
| WO | 2016/145042 A1 | 9/2016 |

OTHER PUBLICATIONS

Search Report for International Application No. PCT/US2018/026982, dated Jul. 24, 2018, 14 pages.

(Continued)

*Primary Examiner* — Julianna N Harvey
*Assistant Examiner* — Christina Negrellirodriguez
(74) *Attorney, Agent, or Firm* — Foley & Lardner LLP

(57) ABSTRACT

A laminar fixation system includes a laminar fixation implant and a laminar fixation implant tensioning tool for use with laminar fixation tape for retaining a spine rod relative to a vertebra of the spine. The laminar fixation implant has a hook at one end thereof that defines an arcuate pocket for holding a spine rod, a threaded angled bore with a set screw that contacts and fixes a spine rod received in the arcuate pocket, a passage extending through the hook for receiving laminar fixation tape, and a fixation plate disposed in a sidewall of the arcuate pocket of the hook and abutting the passage, whereby pressure exerted on the fixation plate by the spine rod presses against and fixes the laminar fixation tape in the passage relative to the laminar fixation implant.

20 Claims, 5 Drawing Sheets

(56) References Cited

U.S. PATENT DOCUMENTS

| | | |
|---|---|---|
| 2013/0268011 A1 | 10/2013 | Rezach et al. |
| 2014/0257401 A1 | 9/2014 | George et al. |
| 2016/0157896 A1 | 6/2016 | Palmer et al. |
| 2016/0242825 A1 | 8/2016 | Simpson et al. |

OTHER PUBLICATIONS

International Search Report and Written Opinion for International Application No. PCT/US2018/026747, dated Jul. 23, 2018, 11 pages.

* cited by examiner

LAMINAR CLAMP TENSIONER AND METHOD

CROSS-REFERENCE TO RELATED APPLICATIONS

This U.S. non-provisional patent application claims the benefit of and/or priority under 35 U.S.C. § 119(e) to U.S. provisional patent application Ser. No. 62/483,762 filed Apr. 10, 2017 titled "Laminar Clamp Tensioner and Method," the entire contents of which is specifically incorporated herein by reference.

FIELD OF THE INVENTION

The present invention relates to systems, implants and methods for orthopedic fixation of the spine and, more particularly, to systems, implants and methods for retaining a spine rod relative to a vertebra of the spine.

BACKGROUND OF THE INVENTION

Spine issues such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spine disorders typically result in symptoms including deformity, pain, nerve damage, and partial or complete loss of mobility. Non-surgical treatments, such as medication, rehabilitation and exercise can be effective, however, may fail to relieve the symptoms associated with these disorders. In some cases, non-surgical treatment is not an option. If non-surgical treatment fails or is not available, surgical treatment is required.

Surgical treatment of the aforementioned spine disorders includes correction, fusion, fixation, discectomy, laminectomy, and implants. Correction treatments used for positioning, alignment and stabilization of the spine employ implants such as spine (vertebral) rods and vertebral bone screw assemblies that provide connection to the spine rod, as well as other implants. Because of complex anatomies, severe spinal deformities, compromised pedicle anatomy, and/or poor vertebral bone quality, vertebral bone screw assemblies cannot be used. In these cases a laminar band and associated implant (a laminar fixation implant) is used to connect the spine rod to a vertebra, wherein the implant attaches to the spine rod and the band is received around the lamina or sub-lamina of the vertebra utilizing the strength of the laminar cortical bone. Most laminar fixation implants are installed using an installation tool specifically designed for the particular laminar fixation implant, creating a laminar fixation system.

While there are many styles of laminar fixation implants and laminar fixation systems, most are generally awkward, cumbersome and/or difficult to effectively use. There is therefore a need for a more efficient laminar fixation implant and/or laminar fixation system.

SUMMARY OF THE INVENTION

A laminar fixation system includes a laminar fixation implant and a laminar fixation implant tensioning tool for use with laminar fixation tape for retaining a spine rod onto the lamina of a vertebra of the spine.

The laminar fixation implant is characterized by a generally rectangular, one-piece body having a hook at one end thereof and defining an arcuate pocket for holding a spine rod, a locking mechanism configured to affix the laminar fixation implant to a spine rod received in the arcuate pocket, a passage extending through the hook from a top of the hook to a lower side of the hook for receiving laminar fixation tape, and a fixation plate disposed in a sidewall of the arcuate pocket of the hook and abutting the passage, whereby pressure exerted on the fixation plate will press against and fix laminar fixation tape in the passage relative to the laminar fixation implant.

In one form, the locking mechanism includes a threaded bore extending through the implant body from the top of the implant body to proximate the arcuate pocket, the threaded bore angled from the top of the implant body towards the arcuate pocket, and a set screw disposed in the threaded bore, the set screw having an angled end that is configured to engage a spine rod held in the arcuate pocket.

The laminar fixation implant body further has a first configured cutout on a first lateral side thereof, and a second configured cutout on a second lateral side thereof. The first and second cutouts are configured to receive first and second retention portions of the laminar fixation implant tensioning tool.

The laminar fixation implant tensioning tool includes a tubular body having a movable carriage situated about the tubular body, the movable carriage having a clamp that is adapted to lock movement of laminar fixation tape and allow freedom of movement of laminar fixation tape received therein. An actuator of the laminar fixation implant tensioning tool is connected to the movable carriage for controlling up and down movement of the carriage with respect to the tubular body. Laminar fixation tape retained by the clamp is tensioned by upward movement of the carriage and loosened by downward movement of the carriage.

Laminar fixation tape in the form of a loop extending from the laminar fixation implant and fixed to the movable carriage via the clamp is tensioned by controlled movement of the carriage.

The laminar fixation implant tensioning tool includes first and second tangs on a lower end of the tubular body that are configured to engage the first and second configured cutouts for releasably holding the laminar fixation implant.

In one form, the actuator of the laminar fixation implant tensioning tool is controlled through rotation of a "T" handle disposed at the upper end of the tubular body.

Further aspects of the present invention will become apparent from consideration of the figures and the following description of the invention. A person skilled in the art will realize that other forms of the invention are possible and that the details of the invention can be modified in a number of respects without departing from the inventive concept. The following figures and description are to be regarded as illustrative in nature and not restrictive.

BRIEF DESCRIPTION OF THE DRAWINGS

The features of the invention will be better understood by reference to the accompanying drawings which illustrate a form of the present invention, wherein.

Figure 1:
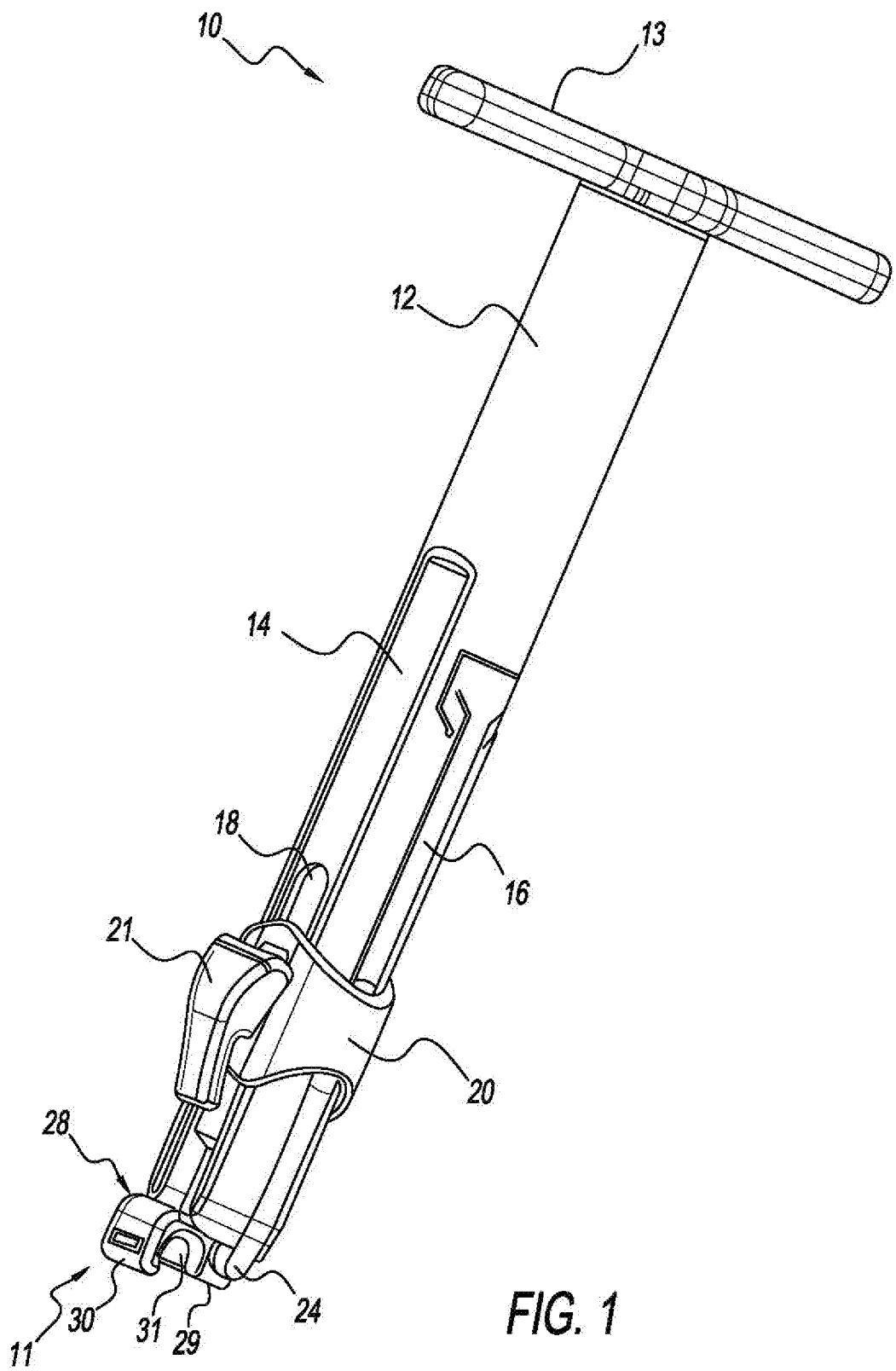
FIG. 1 is an isometric view of the present laminar fixation implant held by the present laminar fixation implant tensioning tool.

It should be appreciated that dimensions of the components, structures, and features of the present laminar fixation system can be altered as desired.

DETAILED DESCRIPTION OF THE INVENTION

Referring to FIGS. 1-5, there is shown a laminar fixation tensioning tool 10 and a laminar fixation implant 11, both fashioned in accordance with the present principles, the laminar fixation implant tensioning tool 10 and the laminar fixation implant 11 comprising a laminar fixation system. The laminar fixation system uses laminar fixation tape B (or laminar fixation band) for retaining a spine rod R (see FIG. 2) relative to a vertebra of the spine (not shown). Particularly, the laminar fixation implant 11 is configured to attach onto a spine rod and be held to the lamina, sub-lamina, or other part of a vertebra (not shown) via laminar fixation tape B (or a laminar fixation band) via a laminar tape loop 1 (see FIG. 5) that wraps around the lamina, sub-lamina, or other part of a vertebra.

The laminar fixation implant 11 is characterized by a generally rectangular body 28 formed of a biocompatible material such as, but not limited to, titanium, stainless steel, an alloy thereof, ceramic, PEEK, other plastics or polymers, or other bio-compatible material having appropriate characteristics for its intended purpose as described herein. The body 28 defines a base 29 and a hook 30 extending from the base 29. The hook 30 defines a rod retention area 31 for receipt of a spine rod (see FIG. 2). A passage or channel 38 extends through the hook 30 from a top of the hook 30 to a lower side of the hook 30. The passage 38 is sized to receive laminar fixation tape (or band) B (see e.g., FIGS. 2, 3, 5). The passage 17 allows the laminar fixation tape to freely pass therethrough in order to form a loop 1 (see FIG. 5) for extending about the laminar or other bony portion of a vertebra (not shown).

Figure 5:
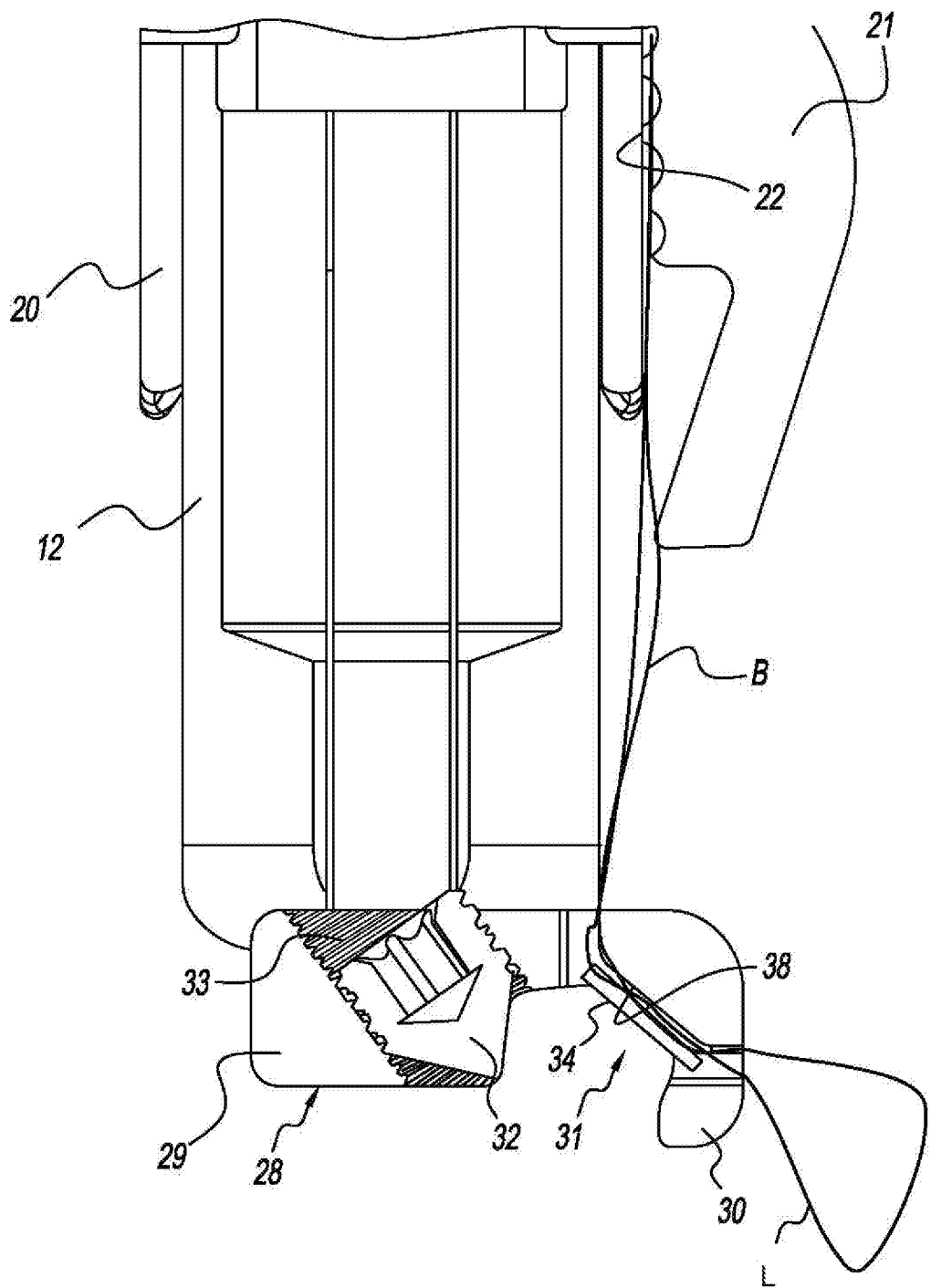
FIG. 5 is an enlarged side sectional view of a bottom portion of the present laminar fixation tensioning tool holding the present laminar fixation implant and shown with laminar fixation tape extending through the passage of the hook to form a laminar attached loop and retained by the fixation plate, the locking clamp of the carriage in a tape locked state.

The base 29 has a first locking mechanism for fixing the implant 11 onto the spine rod (R). A threaded bore 33 is provided in the base 29 extending from a top of the base 29 to a bottom of the base 29. As best seen in FIG. 5, the threaded bore 33 is angled as it extends from the top of the base 29 to the bottom of the base 29 such that the opening at the bottom of the base 29 is adjacent and extends into the rod retention area 31 of the hook 30. A set screw 32 is provided in the threaded bore 33, the set screw 32 having an angled end configured to engage a spine rod held in the arcuate pocket and therefor clamp onto and retain the spine rod by the hook 30.

The laminar fixation implant 11 further has a second locking mechanism for locking/fixing the laminar fixation tape relative to the implant. Particularly, a fixation plate 35 is disposed in a sidewall of the arcuate pocket 31 of the hook 30 and abutting the passage 38, whereby pressure exerted on the fixation plate 35 will press against and fix laminar fixation tape in the passage 38 relative to the laminar fixation implant. Pressure is exerted by a spine rod received in the pocket 31.

The laminar fixation implant 11 has a first cutout 35 on the first lateral side of the base 29 proximate the top of the base 29, and a second cutout (not seen, but opposite the first cutout 35) on the second lateral side of the base proximate the top of the base 29. The first and second cutouts are preferably, but not necessarily, J-shaped and configured to releasably receive retention features (i.e. tangs 24, 25) of the tensioning tool 10.

The laminar fixation tensioning tool 10 includes a tubular body 12 with an actuator therein controlled by the "T" handle 13 disposed at the top of the tubular body 12. The tubular body 12 has a first channel 14 and a second channel 15 opposite the first channel 14, a third channel 16 between the first and second channels 14, 16, and a fourth channel 17 opposite the third channel 16. The channels 14, 15, 16, 17 retain guide members of a carriage 20 disposed on the tubular body 12. The actuator is connected to the carriage 20 internal to the tubular body 12 and to the handle 13, such that rotation of the handle 13 in one direction moves the carriage 20 up the tubular body 13, while rotation of the handle 13 in an opposite direction moves the carriage 20 down the tubular body 13. Upward movement of the carriage 20 tensions the laminar fixation tape while downward movement of the carriage 20 loosens the laminar fixation tape. The bottom end of the tubular body 13 (opposite the handle 13) includes an implant retention portion consisting of the first and second tangs 24, 25 that engage the first and second cutouts of the implant 11.

The carriage 20 includes a clamp 21 pivotally connected at one side thereof, the clamp 21 being of any style such as, but not limited to, a cam lock clamp, the carriage 20 and clamp 21 being or at least a part of a tensioning assembly, portion or mechanism for the laminar fixation tape. The clamp 21 has teeth or the like 22 that provide positive holding of the laminar fixation tape. The tensioning assembly is thus configured to releasably retain a portion of the laminar fixation tape in order to tension the laminar fixation tape looped about the lamina during installation. Once the laminar fixation tape is locked by the clamp, the carriage 20 may be moved as desired to provide a desired tensioning.

Figure 2:
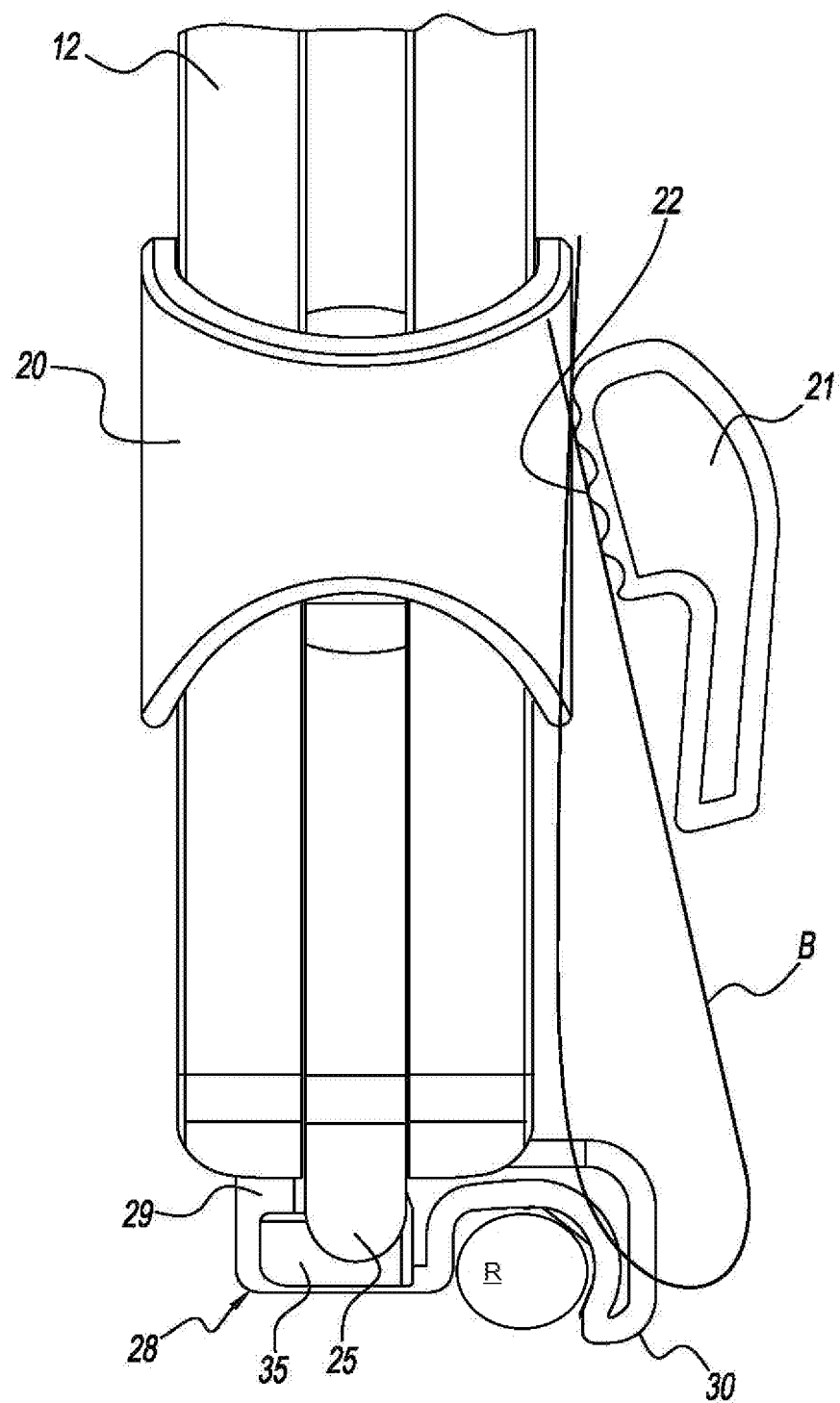
FIG. 2 is an enlarged side view of a bottom portion of the present laminar fixation tensioning tool holding the present laminar fixation implant with a spine rod held within the arcuate pocket of the hook, and shown with laminar fixation tape extending through the passage of the hook and the locking clamp of the tensioning carriage, the locking clamp in a tape unlocked state.
Figure 3:
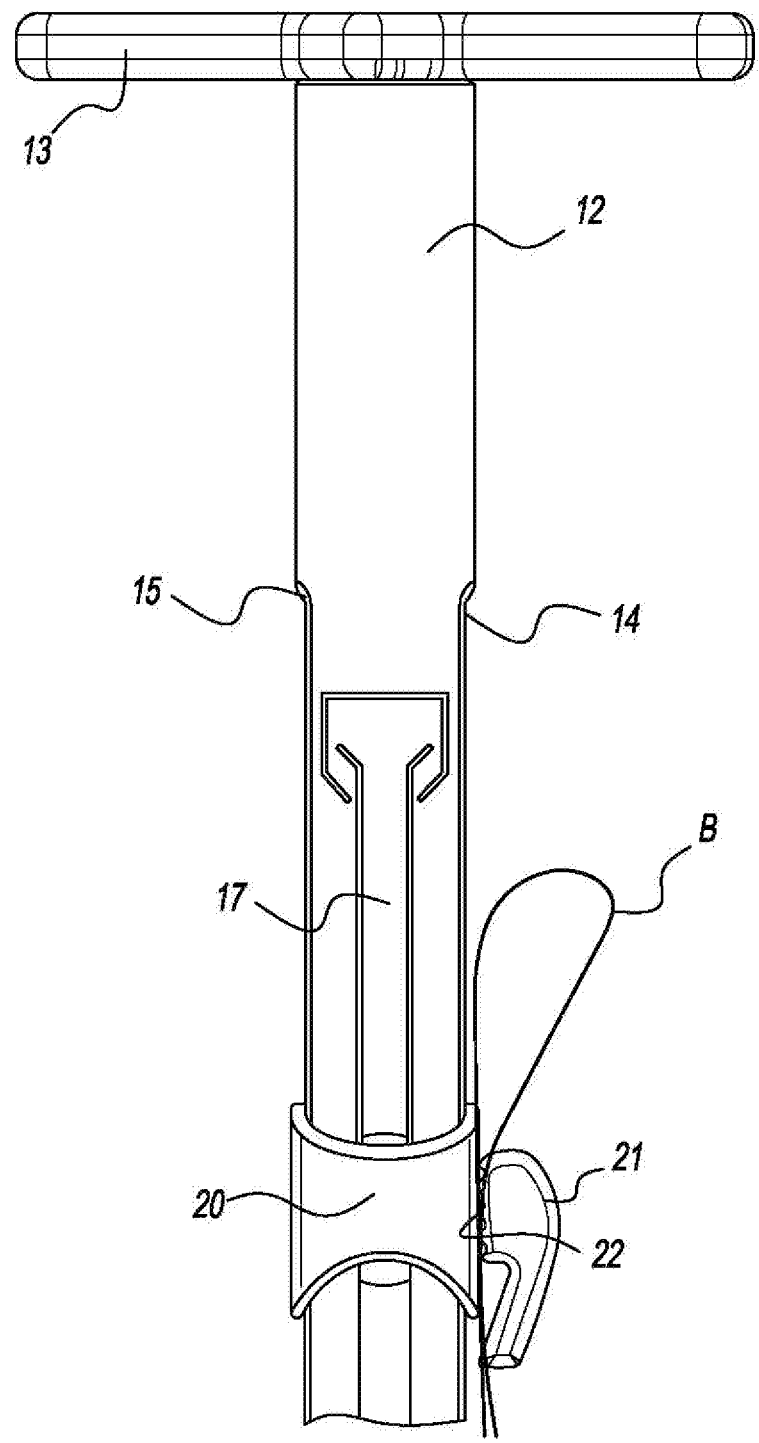
FIG. 3 is a side view of an upper portion of the laminar fixation tensioning tool with laminar fixation tape, the locking clamp in a tape locked state.
Figure 4:
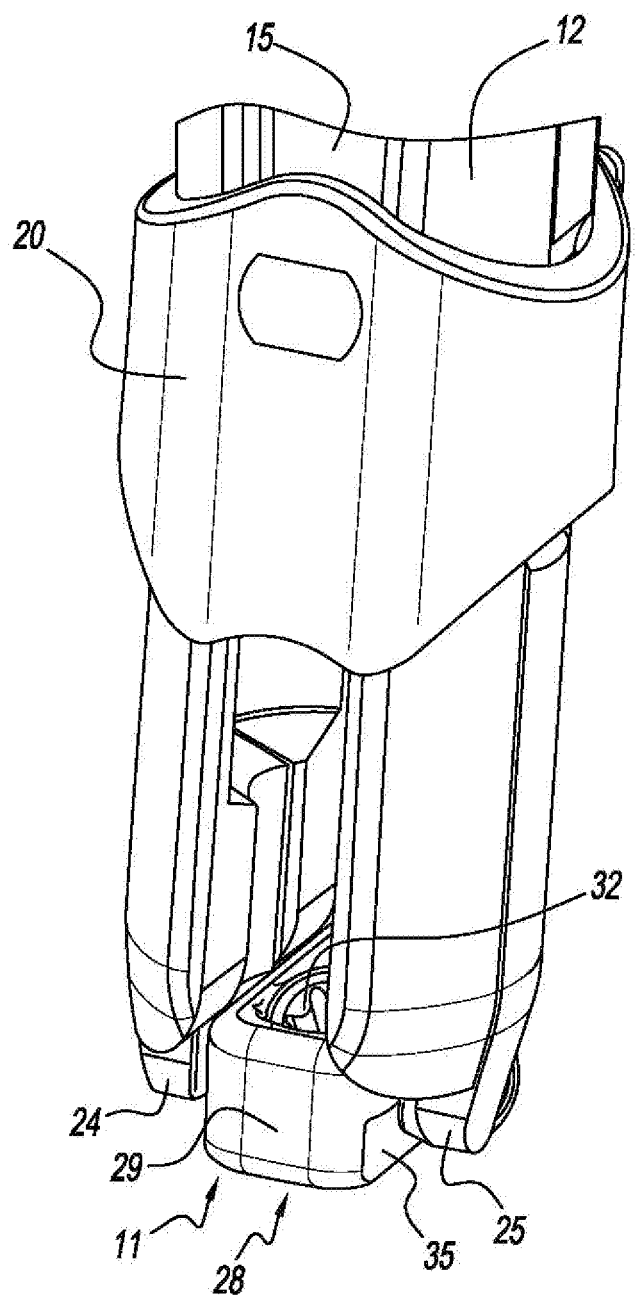
FIG. 4 is an enlarged isometric view of a bottom area of the present laminar fixation tensioning tool holding the present laminar fixation implant.

When the clamp 21 is in the position shown in FIG. 2, the clamping mechanism is in a tape unlocked state or position which allows the laminar fixation tape to freely move therethrough. When the clamp 21 is in the position shown in FIG. 5, the clamping mechanism is in a tape locked state or position which prevents free movement of the laminar fixation tape.

A method of installation includes threading laminar tape through the laminar fixation implant 11, clamping the laminar fixation implant onto a spine rod, threading the laminar fixation tape into the implant, looping the laminar tape around a lamina, sub-lamina or other vertebral bone/bone portion, then tightening the laminar tape accordingly.

It should be appreciated that dimensions of the components, structures, and/or features of the present laminar fixation implant and installation instrument may be altered as desired within the scope of the present disclosure.

What is claimed is:

1. A laminar fixation system for retaining a spine rod relative to a vertebra of the spine, the laminar fixation system comprising:
   a laminar fixation implant having a rectangular body with a hook at one end that defines an arcuate pocket for holding the spine rod, a locking mechanism configured to affix the laminar fixation implant to the spine rod received in the arcuate pocket of the hook, a passage extending through the hook from a top of the hook to a lower side of the hook for receiving laminar fixation tape, and a fixation plate disposed in a sidewall of the arcuate pocket of the hook and abutting the passage, whereby pressure exerted on the fixation plate will press against and fix laminar fixation tape in the passage relative to the laminar fixation implant; and
   a laminar fixation implant tensioning tool having a tubular body, a movable carriage situated about the tubular body, the movable carriage having a clamp that is adapted to lock movement of laminar fixation tape and allow freedom of movement of laminar fixation tape received therein, and an actuator connected to the movable carriage that is adapted to control up and down movement of the carriage with respect to the tubular body, whereby laminar fixation tape retained by the clamp is tensioned by upward movement of the movable carriage and loosened by downward movement of the movable carriage.

2. The laminar fixation system of claim 1, wherein:
   the locking mechanism includes a threaded bore extending through the implant body from the top of the implant body to proximate the arcuate pocket of the hook, the threaded bore angled from the top of the implant body towards the arcuate pocket; and
   the laminar fixation system further includes a set screw disposed in the threaded bore, the set screw having an angled end that is configured to engage a spine rod held in the arcuate pocket.

3. The laminar fixation system of claim 2, wherein the actuator of the laminar fixation implant tensioning tool is controlled through rotation of a "T" handle disposed at an upper end of the tubular body.

4. The laminar fixation system of claim 2, wherein the clamp of the movable carriage comprises a cam lock clamp.

5. A method of retaining a spine rod relative to a vertebra comprising:
   providing a laminar fixation system having:
   a laminar fixation implant having a rectangular body with a hook at one end that defines an arcuate pocket for holding a spine rod, a locking mechanism configured to affix the laminar fixation implant to a spine rod received in the arcuate pocket of the hook, a passage extending through the hook from a top of the hook to a lower side of the hook for receiving laminar fixation tape, and a fixation plate disposed in a sidewall of the arcuate pocket of the hook and abutting the passage, whereby pressure exerted on the fixation plate will press against and fix laminar fixation tape in the passage relative to the laminar fixation implant; and
   a laminar fixation implant tensioning tool having a tubular body, a movable carriage situated about the tubular body, the movable carriage having a clamp that is adapted to lock movement of laminar fixation tape and allow freedom of movement of laminar fixation tape received therein, and an actuator connected to the movable carriage that is adapted to control up and down movement of the carriage with respect to the tubular body, whereby laminar fixation tape retained by the clamp is tensioned by upward movement of the movable carriage and loosened by downward movement of the movable carriage;
   providing laminar fixation tape;
   threading the laminar fixation tape through the passage of the hook of the laminar fixation implant;
   threading the laminar fixation tape through the clamp of the movable carriage;
   looping the laminar fixation tape around a lamina of a vertebra;
   locking movement of the laminar fixation tape by the clamp;
   tensioning the laminar fixation tape by moving the carriage; and
   fixing the laminar fixation tape relative to the laminar fixation implant via the second locking mechanism of the laminar fixation implant through locking a spine rod in the arcuate pocket of the hook via a set screw.

6. The method of claim 5, wherein the actuator of the laminar fixation implant tensioning tool comprises a rotatable "T" handle disposed at an upper end of the tubular body.

7. The method of claim 5, wherein fixing the laminar fixation tape relative to the laminar fixation implant comprises manipulating the set screw such that the set screw contacts the spine rod and causes the spine rod to reposition the fixation plate such that the fixation plate contacts the laminar fixation tape within the passage.

8. A laminar fixation system for retaining a spine rod relative to a vertebra of the spine, the laminar fixation system comprising:
   a laminar fixation implant having a body with a hook at one end that defines an arcuate pocket for holding the spine rod, a spine rod locking mechanism configured to affix the hook to the spine rod received in the arcuate pocket, a channel extending through the hook from a top of the hook to a lower side of the hook for receiving laminar fixation tape, and a laminar fixation tape locking mechanism comprising a fixation plate disposed in a sidewall of the arcuate pocket wherein pressure applied to the fixation plate causes the fixation plate to fix the laminar fixation tape in the channel; and
   a laminar fixation implant tensioning tool having a tubular body, a movable carriage situated about the tubular body, the movable carriage having a clamp that is adapted to lock movement of laminar fixation tape and allow freedom of movement of laminar fixation tape received therein, and an actuator connected to the movable carriage that is adapted to control up and down movement of the carriage with respect to the tubular body, whereby laminar fixation tape retained by the clamp is tensioned by upward movement of the movable carriage and loosened by downward movement of the movable carriage.

9. The laminar fixation system of claim 8, wherein:
   the locking mechanism includes a threaded bore extending through the implant body from the top of the implant body to proximate the arcuate pocket of the hook, the threaded bore angled from the top of the implant body towards the arcuate pocket; and
   the laminar fixation system further includes a set screw disposed in the threaded bore, the set screw having an angled end that is configured to engage a spine rod held in the arcuate pocket.

10. The laminar fixation system of claim 9, wherein the actuator of the laminar fixation implant tensioning tool is controlled through rotation of a "T" handle disposed at an upper end of the tubular body.

11. The laminar fixation system of claim 8, wherein the clamp of the movable carriage comprises a cam lock clamp.

12. The laminar fixation implant of claim 8, wherein the locking mechanism comprises:
   a threaded bore providing fluid communication through the body of the laminar fixation implant, the threaded bore having a first opening disposed adjacent the arcuate pocket; and
   a set screw configured to be received by the threaded bore and protrude from the first opening such that at least a portion of the set screw contacts the spine rod such that the spine rod is retained within the arcuate pocket.

13. A laminar fixation implant for use with a laminar fixation implant system, the laminar fixation implant comprising:
   a body configured to retain a spine rod relative to a vertebra of the spine, the body comprising:
   a hook defining an arcuate pocket configured to receive the spine rod;
   a channel extending through the hook and configured to receive a laminar fixation tape, wherein the laminar fixation tape is configured to be secured to a portion of the vertebra of the spine;
   a fixation plate disposed in a sidewall of the arcuate pocket such that a first surface of the fixation plate is arranged adjacent the laminar fixation tape within the channel and a second surface is arranged within the arcuate pocket and adjacent the spine rod; and
   a locking mechanism configured to secure the laminar fixation implant to the spine rod, wherein the locking mechanism applies a force to the spine rod such that the laminar fixation implant is coupled to the spine rod;
   wherein the force is translated by the spine rod to the second surface of the fixation plate such that the first surface of the fixation plate contacts the laminar fixation tape and retains the laminar fixation tape within the channel.

14. The laminar fixation implant of claim 13, wherein the locking mechanism comprises:
   a threaded bore providing fluid communication through the body of the laminar fixation implant, the threaded bore having a first opening disposed adjacent the arcuate pocket; and
   a set screw configured to be received by the threaded bore and protrude from the first opening such that at least a portion of the set screw contacts the spine rod such that the spine rod is retained within the arcuate pocket.

15. The laminar fixation implant of claim 14, wherein the set screw is configured to apply the force to the spine rod such that the spine rod contacts the second surface of the fixation plate and the first surface of the fixation plate contacts the laminar fixation tape.

16. The laminar fixation implant of claim 14, wherein the laminar fixation implant is configured to function cooperatively with a laminar fixation implant tensioning tool.

17. The laminar fixation implant of claim 16, wherein the laminar fixation implant tensioning tool comprises a clamp configured to lock movement of the laminar fixation tape such that the laminar fixation tape may be adjusted within the channel when the set screw is withdrawn within the threaded bore.

18. The laminar fixation implant of claim 17, wherein the laminar fixation implant tensioning tool comprises an actuator controlled through rotation of a "T" handle disposed at an upper end of a tubular body of the laminar fixation implant tensioning tool.

19. The laminar fixation implant of claim 13, wherein the laminar fixation tape is configured to be secured to a lamina of the vertebra of the spine.

20. The laminar fixation implant of claim 13, wherein the channel is configured to receive a first layer of the laminar fixation tape and a second layer of the laminar fixation tape adjacent the first layer of the laminar fixation tape.

* * * * *